US010018576B2

(12) United States Patent
Herbsommer et al.

(10) Patent No.: US 10,018,576 B2
(45) Date of Patent: Jul. 10, 2018

(54) MATERIAL DETECTION AND ANALYSIS USING A DIELECTRIC WAVEGUIDE

(71) Applicant: Texas Instruments Incorporated, Dallas, TX (US)

(72) Inventors: Juan Alejandro Herbsommer, Allen, TX (US); Robert Floyd Payne, Lucas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 175 days.

(21) Appl. No.: 14/586,842

(22) Filed: Dec. 30, 2014

(65) Prior Publication Data

US 2015/0293039 A1 Oct. 15, 2015

Related U.S. Application Data

(60) Provisional application No. 61/977,418, filed on Apr. 9, 2014.

(51) Int. Cl.
*G01V 3/10* (2006.01)
*G01N 22/00* (2006.01)

(52) U.S. Cl.
CPC .................... *G01N 22/00* (2013.01)

(58) Field of Classification Search
CPC . G01V 3/10; G01V 3/15; G01V 3/104; G01V 3/165; G01V 3/081; G01V 3/08; G01V 3/12; G01V 3/17; G01V 11/00; G01V 13/00; G01V 15/00
USPC ...... 324/636, 641, 754.06, 84, 95, 314, 329, 324/332, 637, 639
See application file for complete search history.

(56) References Cited

U.S. PATENT DOCUMENTS

| | | | | |
|---|---|---|---|---|
| 5,351,521 A | * | 10/1994 | Cracknell | G01N 22/00 324/640 |
| 7,334,451 B1 | * | 2/2008 | Fauveau | G01F 23/284 73/1.73 |
| 8,854,255 B1 | * | 10/2014 | Ehret | G01S 13/538 342/160 |
| 2002/0149377 A1 | * | 10/2002 | Hefti | G01N 22/00 324/636 |

(Continued)

OTHER PUBLICATIONS

"3D Printing", Wikipedia, pp. 1-35, available at http://en.wikipedia.org/w/index.php?title=3D_printing&oldid=624190184 on Sep. 4, 2014.

(Continued)

*Primary Examiner* — Jermele M Hollington
*Assistant Examiner* — Taqi Nasir
(74) *Attorney, Agent, or Firm* — Michael A. Davis, Jr.; Charles A. Brill; Frank D. Cimino (57) ABSTRACT

A dielectric waveguide (DWG) may be used to identify a composition of a material that is in contact with the DWG. A radio frequency (RF) signal is transmitted into a dielectric waveguide located in contact with the material. The RF signal is received after it passes through the DWG. An insertion loss of the DWG is determined. The presence of the material may be inferred when the insertion loss exceeds a threshold value. The composition of the material may be inferred based on a correlation with the insertion loss. Alternatively, a volume of the material may be inferred based on a correlation with the insertion loss.

20 Claims, 10 Drawing Sheets

(56) References Cited

U.S. PATENT DOCUMENTS

| | | | |
|---|---|---|---|
| 2010/0102828 A1* | 4/2010 | Bromberg | B01D 46/0086 324/639 |
| 2011/0095245 A1* | 4/2011 | Munson | C09K 21/02 252/607 |
| 2012/0206253 A1* | 8/2012 | Taniguchi | G01N 33/2835 340/438 |
| 2014/0285277 A1* | 9/2014 | Herbsommer | H01P 3/16 333/1 |
| 2014/0287701 A1 | 9/2014 | Herbsommer et al. | |
| 2015/0295297 A1* | 10/2015 | Cook | H01P 3/122 333/239 |

OTHER PUBLICATIONS

Benjamin Cook, et al, "Metallic Waveguide with Dielectric Core", U.S. Appl. No. 14/498,837, filed Sep. 9, 2014, pp. 1-27.

* cited by examiner

MATERIAL DETECTION AND ANALYSIS USING A DIELECTRIC WAVEGUIDE

CLAIM OF PRIORITY UNDER 35 U.S.C. 119(e)

The present application claims priority to and incorporates by reference U.S. Provisional Application No. 61/977,418 filed Apr. 9, 2014, entitled "Dielectric Constant Detection."

FIELD OF THE INVENTION

This invention generally relates to wave guides for high frequency signals, and in particular to waveguides with dielectric cores.

BACKGROUND OF THE INVENTION

In electromagnetic and communications engineering, the term waveguide may refer to any linear structure that conveys electromagnetic waves between its endpoints. The original and most common meaning is a hollow metal pipe used to carry radio waves. This type of waveguide is used as a transmission line for such purposes as connecting microwave transmitters and receivers to their antennas, in equipment such as microwave ovens, radar sets, satellite communications, and microwave radio links.

A dielectric waveguide employs a solid dielectric core rather than a hollow pipe. A dielectric is an electrical insulator that can be polarized by an applied electric field. When a dielectric is placed in an electric field, electric charges do not flow through the material as they do in a conductor, but only slightly shift from their average equilibrium positions causing dielectric polarization. Because of dielectric polarization, positive charges are displaced toward the field and negative charges shift in the opposite direction. This creates an internal electric field which reduces the overall field within the dielectric itself. If a dielectric is composed of weakly bonded molecules, those molecules not only become polarized, but also reorient so that their symmetry axis aligns to the field. While the term "insulator" implies low electrical conduction, "dielectric" is typically used to describe materials with a high polarizability; which is expressed by a number called the dielectric constant ($\epsilon k$). The term insulator is generally used to indicate electrical obstruction while the term dielectric is used to indicate the energy storing capacity of the material by means of polarization.

The electromagnetic waves in a metal-pipe waveguide may be imagined as travelling down the guide in a zig-zag path, being repeatedly reflected between opposite walls of the guide. For the particular case of a rectangular waveguide, it is possible to base an exact analysis on this view. Propagation in a dielectric waveguide may be viewed in the same way, with the waves confined to the dielectric by total internal reflection at its surface.

BRIEF DESCRIPTION OF THE DRAWINGS

Particular embodiments in accordance with the invention will now be described, by way of example only, and with reference to the accompanying drawings.

Other features of the present embodiments will be apparent from the accompanying drawings and from the detailed description that follows.

DETAILED DESCRIPTION OF EMBODIMENTS OF THE INVENTION

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Figure 1:
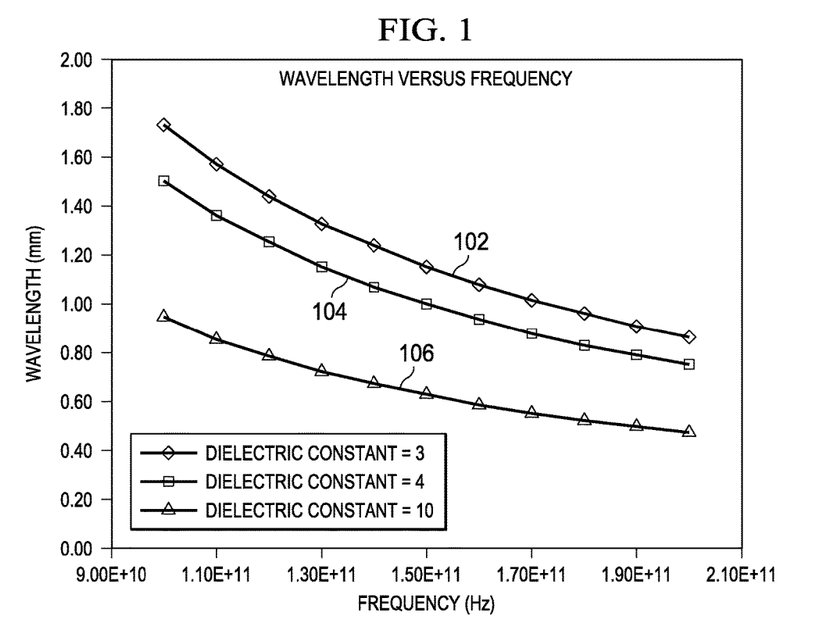
FIG. 1 is a plot of wavelength versus frequency through materials of various dielectric constants.

As frequencies in electronic components and systems increase, the wavelength decreases in a corresponding manner. For example, many computer processors now operate in the gigahertz realm. As operating frequencies increase to sub-terahertz frequencies, the wavelengths become short enough that signal lines that exceed a short distance may act as an antenna and signal radiation may occur. FIG. 1 is a plot of wavelength versus frequency through materials of various dielectric constants. Plot line 102 represents material with dielectric constant of 3, plot line 104 represents material with dielectric constant of 4, and plot line 106 represents material with dielectric constant of 10. As illustrated by plot 102 which represents a material with a low dielectric constant of 3, such as a printed circuit board, a 100 GHz signal will have a wavelength of approximately 1.7 mm. Thus, a signal line that is only 1.7 mm in length may act as a full wave antenna and radiate a significant percentage of the signal energy.

Waves in open space propagate in all directions, as spherical waves. In this way they lose their power proportionally to the square of the distance; that is, at a distance R from the source, the power is the source power divided by R2. A wave guide may be used to transport high frequency signals over relatively long distances. The waveguide confines the wave to propagation in one dimension, so that under ideal conditions the wave loses no power while propagating. Electromagnetic wave propagation along the axis of the waveguide is described by the wave equation, which is derived from Maxwell's equations, and where the wavelength depends upon the structure of the waveguide, and the material within it (air, plastic, vacuum, etc.), as well as on the frequency of the wave. Commonly-used waveguides are only of a few categories. The most common kind of waveguide is one that has a rectangular cross-section, one that is usually not square. It is common for the long side of this cross-section to be twice as long as its short side. These are useful for carrying electromagnetic waves that are horizontally or vertically polarized.

For the exceedingly small wavelengths encountered for sub-THz radio frequency (RF) signals, dielectric waveguides perform well and are much less expensive to fabricate than hollow metal waveguides. Furthermore, a metallic waveguide has a frequency cutoff determined by the size of the waveguide. Below the cutoff frequency there is no propagation of the electromagnetic field. Dielectric waveguides have a wider range of operation without a fixed cutoff point.

However, a signal travelling through a dielectric waveguide (DWG) may produce a small field outside of the DWG that may be affected by external influences. This exterior influence may be just simple handling or a finger touching the dielectric waveguide, for example. Testing has indicated that if not properly isolated, a simple touch of a finger to the exterior of a dielectric waveguide may cause a major degradation of the signal. This effect may be used to detect and analyze a liquid or solid material that is in the vicinity of the DWG based on the dielectric constant value of the material, as will be described in more detail below.

Figure 2:
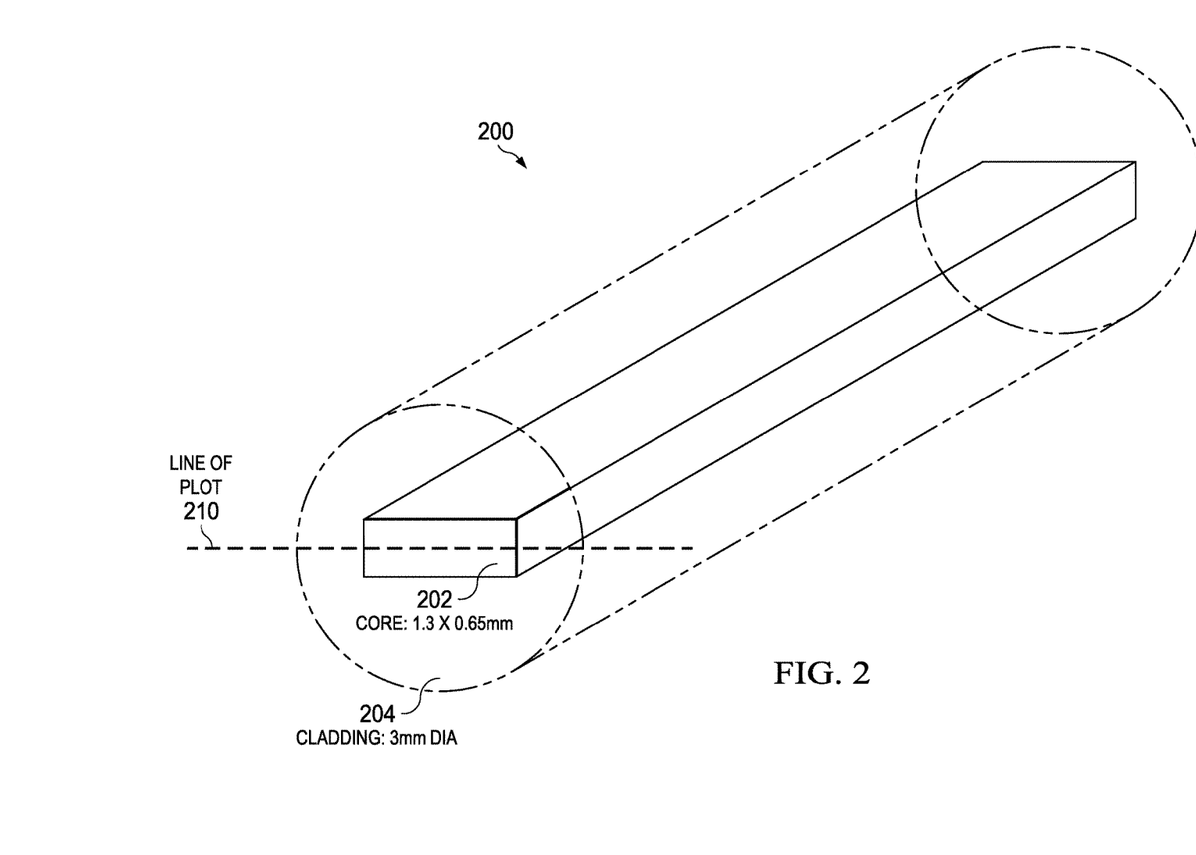
FIG. 2 illustrates an example dielectric waveguide (DWG)

FIG. 2 illustrates an example dielectric waveguide 200. A flexible waveguide configuration may have a core member 202 made from flexible dielectric material with a high dielectric constant ($\varepsilon k1$) and be surrounded with a cladding 204 made from flexible dielectric material with a low dielectric constant, ($\varepsilon k2$). While theoretically, air could be used in place of the cladding, since air has a dielectric constant of approximately 1.0, any contact by humans, or other objects may introduce serious impedance mismatch effects that may result in signal loss or corruption. Therefore, typically free air does not provide a suitable cladding.

For sub-terahertz signals, such as in the range of 130-150 gigahertz, an oblong core dimension of approximately 0.65 mm×1.3 mm works well. As frequency increases, wave length decreases and the physical size of the dielectric core may also be reduced for higher frequency signals. In general, good performance may be obtained as long as the core size is selected to have a dimension that is in the range of approximately 0.3 to 3× of the wavelength of a target signal that is to be transmitted through the DWG. The design of a DWG for a particular target signal frequency and wavelength may be adjusted to optimize attenuation and dispersion by selecting a size within this range, for example.

In general there is no golden rule about the dimensions of the DWG cross section or core dimensions. For a given set of materials, either multimode or mono-mode transmission may occur within a dielectric waveguide. This depends on the dimensions of the core. For example, using HDPE (high density polyethylene) for the core and Polypropylene for the cladding with a core dimension smaller than 0.45 mm×0.9 mm for a signal frequency of approximately 140-200 GHz will result in a mono-mode dielectric waveguide. Such a mono-mode DWG only has one mode of propagation but does not have a cutoff frequency. However it has an important dispersion at lower frequencies. A mono-mode DWG is good for applications in which inter-mode transfer of energy is not wanted. Multimode transmission, on the other hand, may have many modes of signal propagation; however, each mode may have a different cutoff frequency.

Dispersion results in a delay that varies with frequency. It will also change with the dielectric constants of the core, cladding, and surroundings. For the measurement system disclosed herein, it is preferable that the delay to be independent of frequency so that precise control of the frequency of the transceiver systems is not required.

While a rectangular cross section for core 202 is illustrated in this example, various oblong cross sections may be used, such as: rectangular, an oval, elliptical, a rectangle with rounded corners, etc., for example. In this example, an aspect ratio for the width W to the height H is two and produces good multimode operation of the DWG. However, in other embodiments the aspect ratio may be somewhat less than or somewhat greater than two, for example, and still produce good multimode operation.

In this example, cladding 204 has a circular cross section with a diameter of approximately 3 mm. Simulations have shown that the insertion loss produced by a DWG is less when the cross sectional shape of the cladding is different from the cross sectional shape of the core. Thus, in this example a core with a rectangular cross section is combined with a cladding having a circular cross section. Other embodiments may use other combinations of core and cladding cross sectional shapes to produce a low insertion loss.

In this example, the dielectric constant of the core material will typically be in the range of 3-12, while the dielectric constant of the cladding material will typically be in the range of 2.5-4.5.

DWG 200 may be fabricated using standard manufacturing materials and fabrication techniques, such as by using drawing, extrusion, or fusing processes, for example, which are all common-place to the manufacture of plastics.

Figure 3:
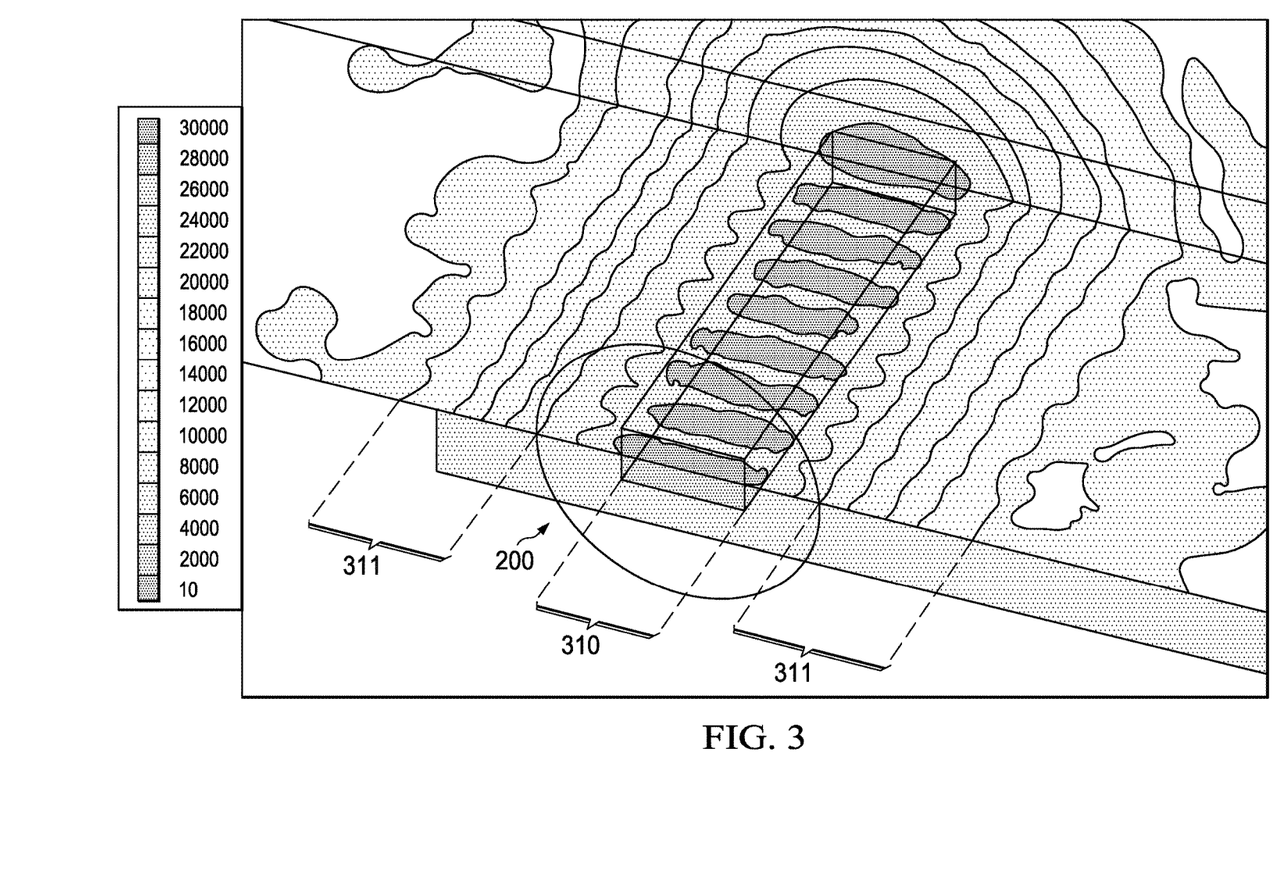
FIG. 3 is a simulation illustrating electric fields created by the propagation of a signal through the DWG of FIG. 2.

FIG. 3 is a simulation illustrating electric fields created by the propagation of a signal through the DWG of FIG. 2. In a dielectric waveguide the electromagnetic fields are concentrated in the core of the DWG as illustrated at 310 and decays in the cladding with a leakage field outside the cladding, referred to as an evanescent field, as illustrated at 311.

Figure 4:
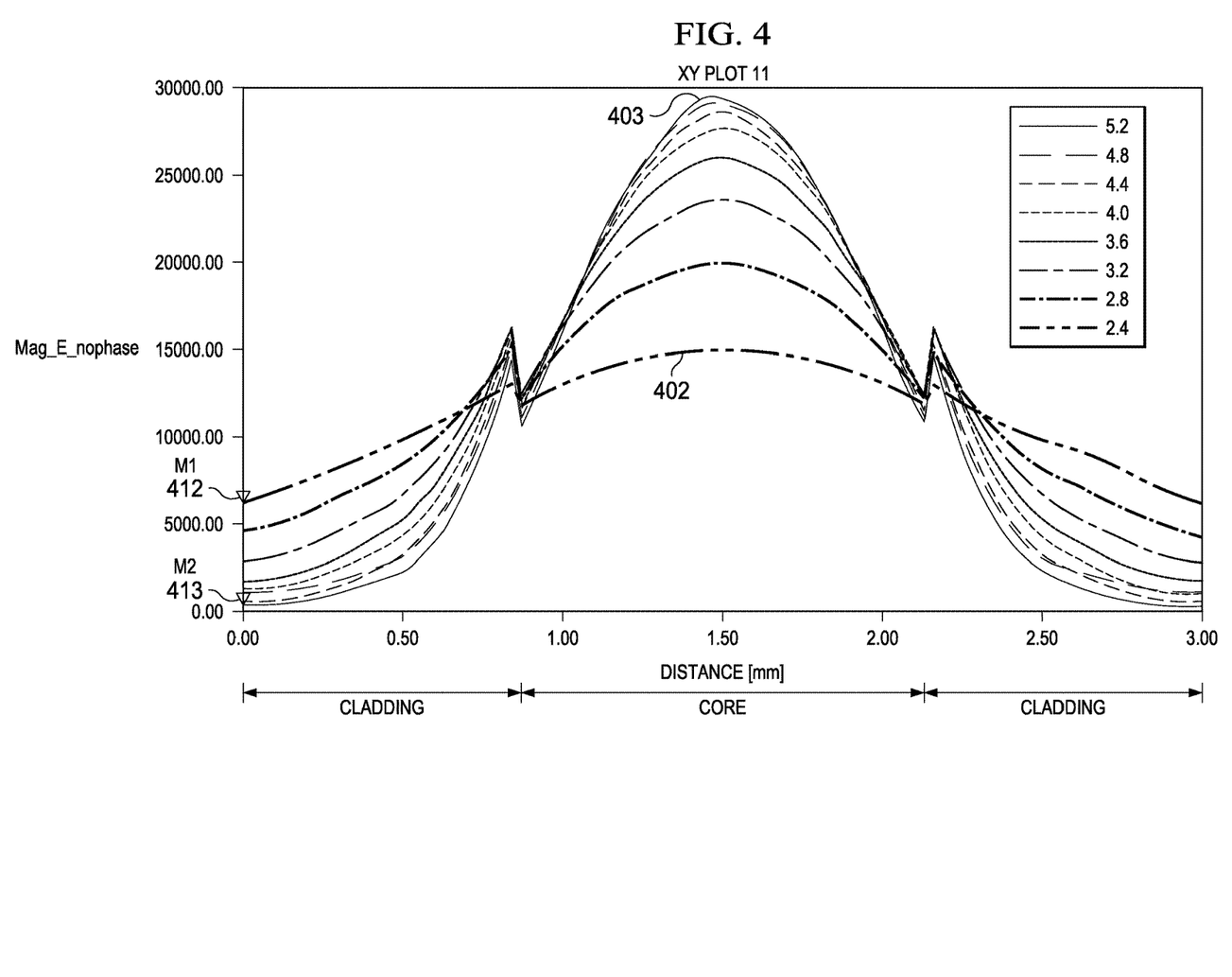
FIG. 4 is a plot illustrating field strength across a DWG with various ratios of dielectric constants between the core and cladding.

FIG. 4 is a plot illustrating field strength across a set of DWGs with various ratios of dielectric constants between the core and cladding. As mentioned above, the dielectric constant of the core material may typically be in the range of 3-12, while the dielectric constant of the cladding material may typically be in the range of 2.5-4.5, for example. The DWG represented by plot line 402 may have a core dielectric constant of 6 and a cladding dielectric constant of 2.5, for example, which provides a ratio of 2.4. Similarly, the DWG represented by plot line 403 may have a core dielectric constant of 12 and a cladding dielectric constant of 2.3, for example, which provides a ratio of 5.2. The other plot lines represent other example combinations of dielectric values that provide ratios of 2.8, 3.2, 3.6, 4.0, 4.4, and 4.8, for example.

As discussed above, Maxwell's equations may be used to determine that the field strength in the DWG drops off exponentially in the cladding region, as illustrated by the plots. With a low dielectric constant ratio, the field strength is more dispersed and is therefore higher at the boundary of the cladding, as indicated at point 412 for DWG 402. For a higher dielectric constant ratio, the field strength is more peaked in the center of the core and less disbursed and is therefore lower at the boundary of the cladding, as indicated at point 413 for DWG 403.

Since the electric field drops of exponentially, there will always be some amount of evanescent wave travelling on the outer surface of the DWG. When the amount of evanescent wave on the surface of the DWG is low enough, such as indicated at 413, then there may not be much interaction with external objects coupling to the transmitted signal. However, when there is significant field strength at the edge of the cladding, there is more opportunity for coupling of the signal to an external object, such as a material that is touching the DWG. For example, water may act as a dielectric with a higher dielectric constant value than air, which is 1.0. This may cause water, for example, to cause a local disturbance in the field at the point of contact and in turn cause a reflection down the DWG that may seriously degrade the signal that is being transmitted through the DWG.

As can be deduced from the plots of FIG. 4, if the cladding is thick enough, then the evanescent wave may be reduced enough that coupling to an external object may not have much effect. Therefore, a DWG that has a relatively thin cladding and/or a low ratio between the dielectric value of the core and cladding may be useful for sensing and detecting material that surrounds at least a portion of the DWG.

Figure 5:
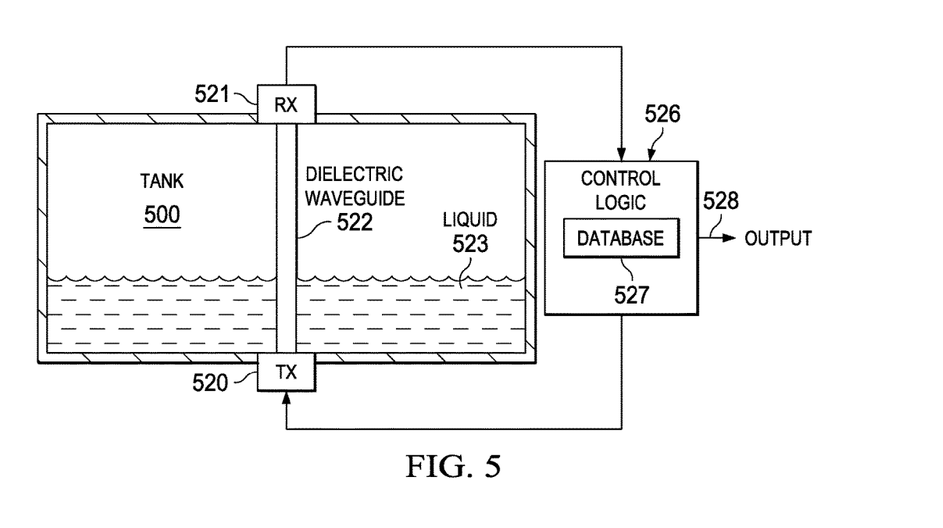
FIGS. 5-6 are example tanks in which a DWG is used to detect and analyze the contents of the tank.

FIG. 5 is an example tank 500 in which a DWG 522 may be used to detect and analyze the contents of the tank. A standard level sensor is designed to detect a quantity of material inside a tank or a reservoir but not the quality of it. Detection of counterfeit liquids and solids inside a tank may be done using a DWG to probe the contents of the tank, for example.

In this example, transmitter (TX) 520 and receiver (RX) 521 are located on opposite sides of the tank. In this example, a radio frequency (RF) signal may be launched from transmitter 520 into DWG 522, propagate through DWG 522, and be received by receiver 521. DWG 522 is positioned vertically within tank 500 so that any material, such as liquid 523, will surround a least a portion of DWG 522.

Control logic 526 is configured to instruct TX 520 to launch a signal into DWG 522 at a defined amplitude. Depending on the application, a fixed frequency signal may be launched, or a range of frequencies may be launched sequentially, randomly, or in some other arrangement, for example. Control logic 526 may instruct RX 521 to measure the amplitude of a received signal. Control logic 526 may then determine insertion loss attributable to DWG 522. Control logic 526 may then consult a data base 527 to determine what type of liquid is present in tank 500 based on the detected insertion loss, for example. An output signal 528 may then be sent to a host system for further action based on the results of the analysis, for example.

Control logic 526 may be a stand-alone module, or may be packaged together with either TX 520 or RX 521, for example. Control logic 526 may be implemented various manners, such as: a microcontroller or other programmable processing unit, dedicated logic, etc., for example. Each transceiver 520, 521 may contain a PWB or other type substrate on which are mounted one or more integrated circuits that produce or receive a sub-terahertz signal that is coupled to DWG 522.

Figure 6:
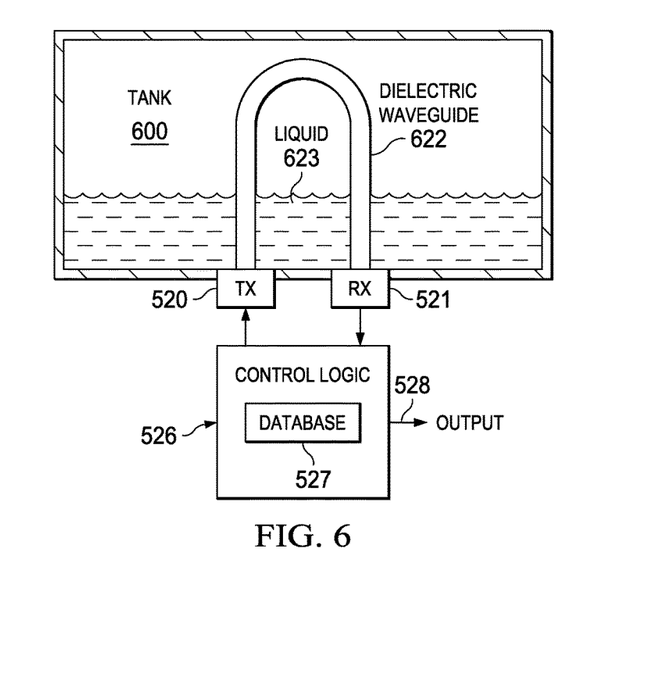

FIG. 6 is another example tank 600 in which a DWG 622 may be used to detect and analyze the contents of the tank. In this example, TX 520 and RX 521 are located on the same side of the tank. In this example, an RF signal may be launched from transmitter 520 into DWG 622, propagate through DWG 622, and be received by receiver 521. DWG 622 is positioned vertically within tank 600 so that any material, such as liquid 623, will surround a least a portion of DWG 622.

Figure 14:
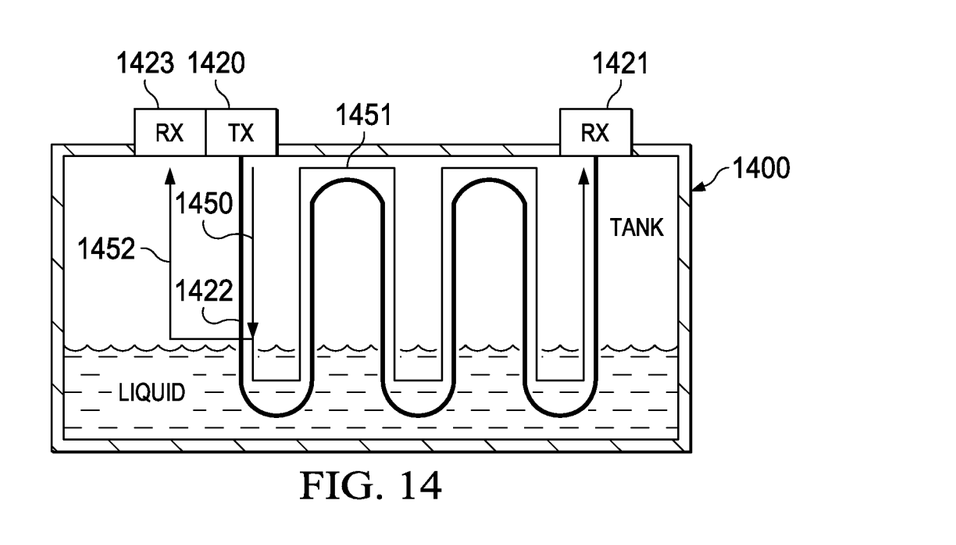
FIG. 14 is an example of another sensor configuration.

In other examples, the DWG may be configured in different positions and arrangements, as long as at least a portion of the DWG is arranged so that the material in the tank will contact it. FIG. 14 illustrates another example of a tank 1400 in which DWG 1422 is configured to have several loops that may be in contact with liquid within tank 1400. Configurations with multiple loops may enhance overall sensitivity by maximizing the length of the DWG that is in contact with the contents of the tank, for example.

In some examples, the DWG may be mounted on a side of the tank, for example; in which case the contents of the tank may contact only one side of the DWG.

A practical example is a system urea-water that is used in the new diesel engines to eliminate pollutant released in the atmosphere. A typical Aqueous Urea Solution is made with 32.5% high-purity urea (AUS 32) and 67.5% deionized water, for example.

Diesel engines can be run with a lean burn air-to-fuel ratio (over-stoichiometric ratio), to ensure the full combustion of soot and to prevent the exhaust of unburnt fuel. The excess of oxygen necessarily leads to generation of nitrogen oxides (NOx), which are harmful pollutants, from the nitrogen in the air. Selective catalytic reduction is used to reduce the amount of NOx released into the atmosphere. Urea-water mixture is injected into the exhaust pipeline; the aqueous urea vaporizes and decomposes to form ammonia and carbon dioxide. Within the SCR catalyst, the NOx are catalytically reduced by the ammonia (NH3) into water (H2O) and nitrogen (N2), which are both harmless; and these are then released through the exhaust.

It is very important to check that the material filling the urea-water tanks is the right mixture and not just water, for example, that could be used to counterfeit the Aqueous Urea Solution.

By measuring the attenuation of a signal propagating along DWG 522 or 622 between TX 520 and RX 521 and knowing the level of the tank, it can be determined if the liquid is counterfeit or not. The level of the liquid may be measured independently using a simple floating level detector, for example.

Figure 7:
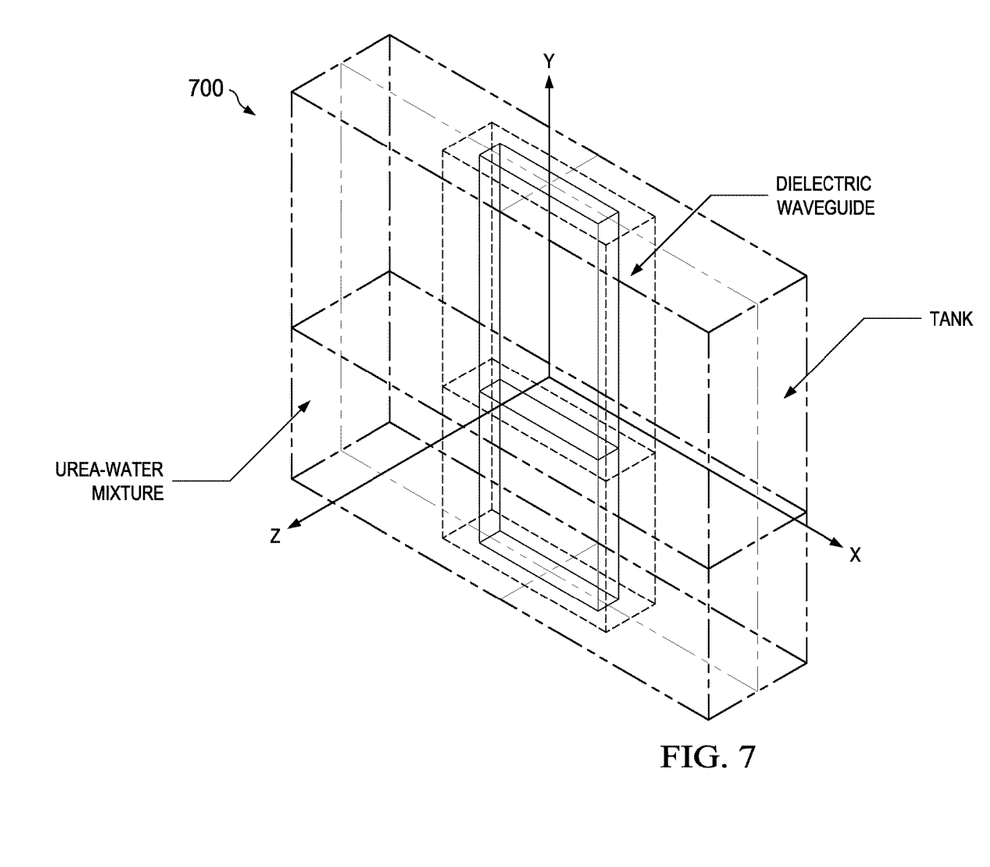
FIG. 7 is an example of a finite element model of a tank.

FIG. 7 is an example of a finite element model of a tank. This example is an HFSS model of a tank with a dielectric waveguide running between the ends of the tank. HFSS is a commercial finite element method solver for electromagnetic structures from Ansys. The acronym originally stood for high frequency structural simulator. It is one of several commercial tools used for antenna design, and the design of complex RF electronic circuit elements including filters, transmission lines, and packaging. While HFSS is used for this example, other known or later developed finite analysis programs may be used to produce a set of useful data.

In this example, the tank is filled at 37.5% with a simulated mix of water and urea. An electromagnetic finite element analysis is done in order to obtain the insertion loss for different mixtures of urea-water solution. In the example, the HFSS analysis was performed for a range of frequencies from 120 to 160 GHz for several mixtures of urea-water.

Figure 8:
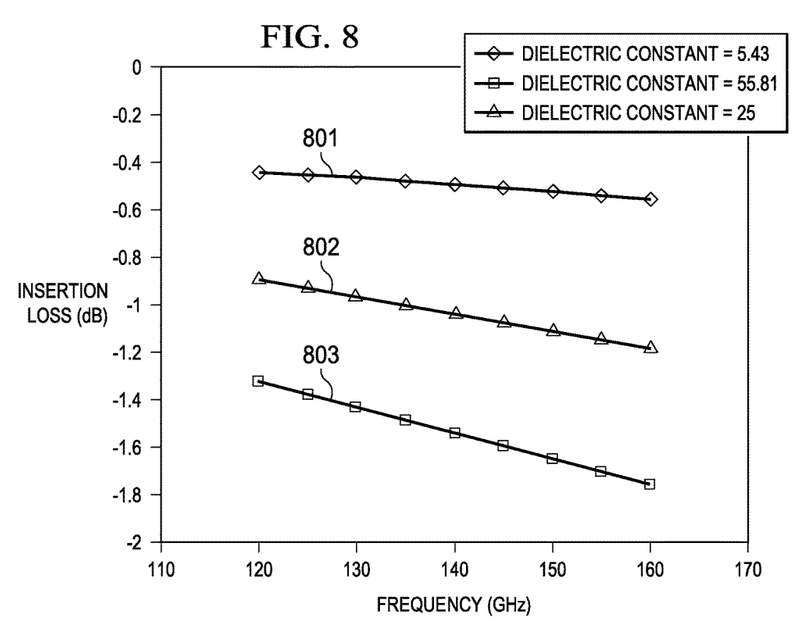
FIG. 8 is a plot illustrating insertion loss in a DWG vs frequency when surrounded by materials with differing dielectric constant values.

FIG. 8 is a plot illustrating insertion loss in a DWG vs frequency when surrounded by materials with differing dielectric constant values, using the simulated tank of FIG. 7 In this example, plot line 801 illustrates total insertion loss for the DWG within the simulated tank vs signal frequency when the DWG is surrounded to a depth of 37.5% by a material having a dielectric constant value of approximately 5. Similarly, plot line 802 illustrates the entire insertion loss vs signal frequency when the DWG is surrounded by a material having a dielectric constant value of 25 and plot line 803 illustrates insertion the entire insertion loss vs signal frequency when the DWG is surrounded by a material having a dielectric constant value of approximately 56. It is clear from the plot that there is a substantial variation of the insertion loss with the dielectric constant of the mixture. This confirms that the evanescent fields are able to detect the dielectric constant of the mixture in the tank.

Figure 9:
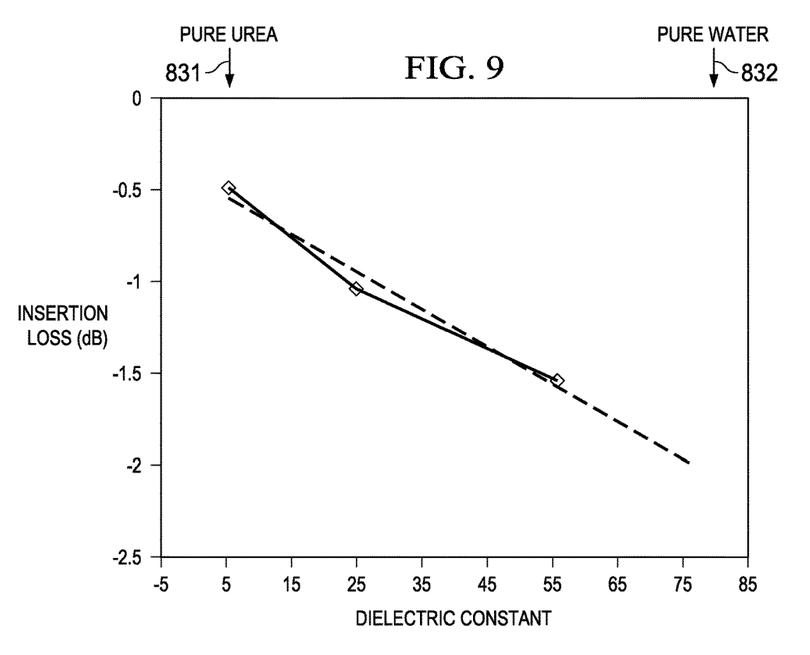
FIG. 9 is a plot illustrating insertion loss in a DWG at a fixed frequency when surrounded by materials with differing dielectric constant values.

FIG. 9 is a plot illustrating insertion loss in a DWG for a fixed frequency when surrounded by materials with differing dielectric constant values based on data from FIG. 8. The variation between pure water indicated at 831 and pure urea indicated at 832 is approximately 1.5 dB change in insertion loss for the condition of the tank being 37.5% full of liquid and the DWG being configured in a straight line.

For a complete solution, a series of HFSS simulations may be performed for different levels of liquid to produce a family of curves that completely characterize the tank and DWG system. During actual operation, control logic may interpolate between the various curves for a specific detected liquid level.

Similarly, a different set of HFSS simulations may be performed for a different DWG and tank configuration, such as the configuration illustrated in FIG. 6, for example.

This is just an example of a system where it is important to detect counterfeit filling of a tank. Many types of systems may use the same technology in order to detect incorrect fluids or solids in a reservoir, for example.

In another embodiment, the amount of material within a tank may be inferred based upon changes in dielectric values that affect insertion loss to a signal propagating through a DWG within a tank. In this example, a set of HFSS simulations may be performed to determine insertion loss for various percentages of fullness in the tank for an expected type of material. The insertion loss will be higher when the tank is full as compared to when the tank is empty, for example. In some applications, a tank will be considered empty when only air is present. However, in other applications a tank may be considered empty when the tank holds a gas, such propane for example, and the amount of gas is reduced to a low density, for example. Therefore, it may be inferred that the tank is approximately empty when the insertion loss is below a threshold value, for example.

In another embodiment, a dielectric constant may be determined using a similar hardware configuration via a time of flight measurement. In this case, referring back to FIG. 5, control logic 526 may generate timing information to mark a start time for a signal transmitted by TX 520 and timing information to indicate when the signal was received by RX 521. This may be done by sending a reference signal to both TX 520 and RX 521. Comparator logic coupled to RX 521 may then determine flight time of the signal through DWG 522, for example. Propagation delay of a signal through DWG 522 may be affected by the material surrounding DWG in the same manner that insertion loss is affected due to changes in the dielectric constant of the material surrounding DWG 522. Therefore, the dielectric constant of the surrounding material may be inferred based on the time of flight information.

Because the time of flight is affected by the material surrounding the DWG, the signal sent through the DWG by TX 1420 may see an impedance discontinuity at the interface between a liquid in the bottom of the tank and a gas, such as air, in the top of the tank, as illustrated in FIG. 14. This discontinuity may cause a signal reflection 1452 that may be used to determine the level of liquid in the tank by using a process similar to a time domain reflectometry (TDR). A TDR measures reflections along a conductor. In order to measure those reflections, the TDR will transmit an incident signal onto the conductor and listen for its reflections. If the conductor is of a uniform impedance and is properly terminated, then there will be no reflections and the remaining incident signal will be absorbed at the far-end by the termination. However, if there are impedance variations, then some of the incident signal may be reflected back to the source. A TDR is similar in principle to radar. In a similar manner, signal reflections 1452 in the DWG caused by the liquid-gas boundary may be received by a second receiver 1423 and may used to determine the level of liquid in a tank. In this example, both the level of a liquid in the tank and the composition of the material within the tank may be determined by analysis of a signal 1450 transmitted by TX 1420 through the DWG, a portion 1451 of which is received by RX 1421 and a reflected portion 1452 of which is received by RX 1423.

It is also possible to use a pulse based measurement, analogous to a captive radar system. In this case, the pulse is confined to the DWG, which allows a pulse based measurement to determine the depth of the liquid based on the reflection of the pulse back from the interface of the DWG surrounded by air and the DWG surrounded by liquid. This could be done with a traditional radar system, albeit at much higher power levels since the DWG confines and guides the RF energy to a single point transition rather than the broad surface of the liquid/air interface.

As illustrated by the plots, the evanescent field is sensitive to the material present outside the DWG. It may be said that the DWG is able to probe the material outside it through the evanescent electromagnetic fields. The detection can be made by measuring the insertion loss of a signal travelling through the DWG from a transmitter (TX) to a receiver (RX). Other prior art technologies may use capacitive detection of the dielectric constant of the liquids and solids. However the problem with a capacitive detection is that a substantial voltage needs to be applied in order to make the detection and this poses a risk of arcing and/or electrostatic charging which it is not advisable in many systems where content analysis would be useful.

The DWGs described in the above examples may be rigid or flexible. Various configurations of dielectric waveguides and interconnect schemes are described in US Patent Publication number 2014-0287701, filed Apr. 1, 2013, entitled "Integrated Circuit with Dipole Antenna Interface for Dielectric Waveguide" by Juan Herbsommer, et al, and are incorporated by reference herein. Various antenna configurations for launching and receiving radio frequency signals to/from a DWG are also described therein and are incorporated by reference herein.

Figure 10:
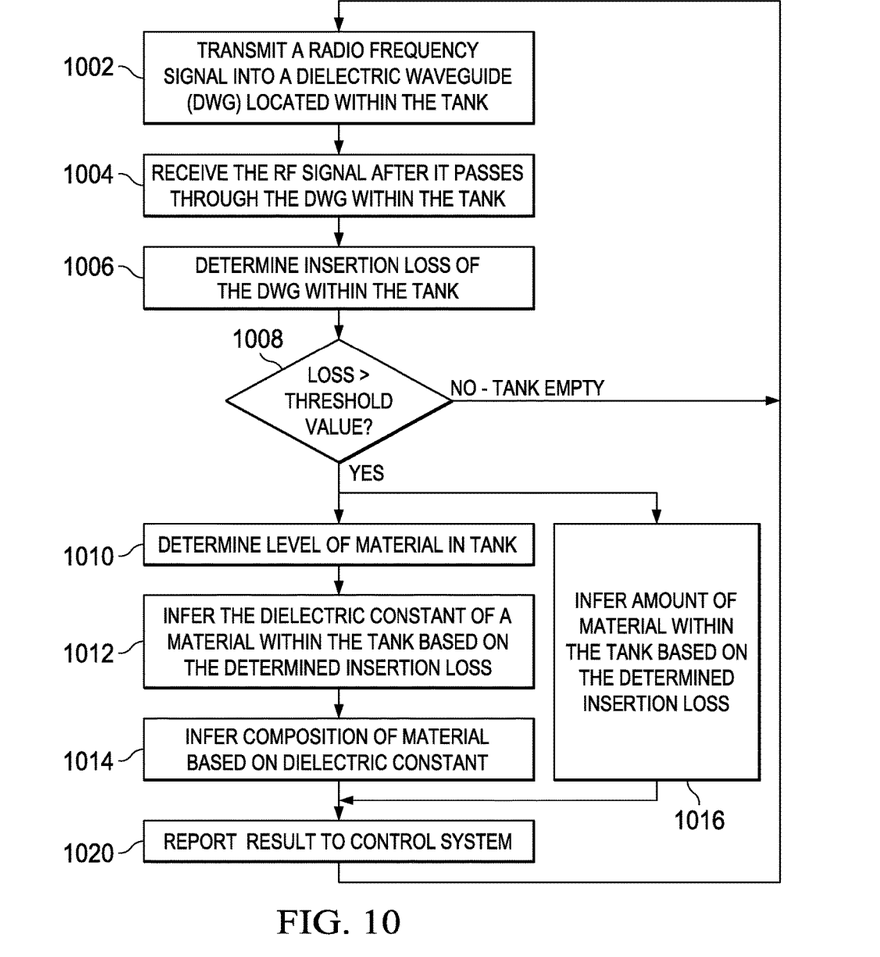
FIG. 10 is a flow chart illustrating use of a DWG in a system to detect and analyze the contents of a tank.

FIG. 10 is a flow chart illustrating use of a DWG in a system to detect and analyze the contents of a tank. In this example, the tank may be similar to those described in FIGS. 5 and 6, for example. The DWG may be any form of flexible of rigid DWG as described in more detail above, for example.

Once the system is turned on, a sub-terahertz RF signal may be generated by an IC in TX 520. The RF signal is then launched 1002 into the DWG using various coupling techniques, such as described in US Patent Publication 2014-0287701, for example.

RX 521 may then capture 1004 the radiated RF signal from the DWG. Control logic may then determine 1006 an insertion loss of the DWG within the tank by determining an amplitude of the received signal and comparing it to a determined amplitude of the signal that was transmitted from TX 520. Alternatively, control logic may then determine 1006 a propagation delay of the signal as it travels through the DWG, as described in more detail above.

As described in more detail above, an evanescent wave traveling on a surface of the DWG may be attenuated by interacting with the material within the tank that is in contact with the DWG or in proximity to the DWG. Attenuation of the evanescent wave will also affect the insertion loss and propagation time of the signal as it propagates through the DWG. A threshold value of attenuation and/or propagation delay may be determined when the tank is empty. This may be done during a calibration operation by the control logic, for example. In another embodiment, the threshold may be determined using simulation or experiments and a representative threshold value stored in database 527 that is coupled to control logic 526, for example.

When the insertion loss or propagation delay is less than the threshold value, then it may be inferred that the tank is empty, as indicated at 1008. In this case, the system may continue to monitor the insertion loss. However, when the insertion loss or propagation delay exceeds the threshold value, then detection and analysis of the material within the tank may proceed.

In some embodiments, another sensor may be provided to determine 1010 a level of the material within the tank. This may be a simple float sensor, optical sensor, ultrasound sensor, infrared sensor, etc., for example. Based on the level of the material in the tank, a dielectric constant value may be inferred 1012 based on the determined insertion loss by consulting a database, such as database 527, for example. As explained above, database 527 may contain tables or other data organizations that correlate insertion loss or propagation delay to dielectric value of the material in the tank. Furthermore, the composition of the material may be inferred 1014 based on the dielectric constant by again consulting the database. Alternatively, the database may be arranged to allow the composition of the material to be inferred directly from the insertion loss value or from the propagation delay value, for example. As explained above, the database information may be determined using simulations, or may be based on experimental lab work, for example.

In some embodiments, a dielectric constant value may be inferred 1016 based on the determined insertion loss or propagation delay by consulting a database, such as database 527, for example. As explained above, database 527 may contain tables or other data organizations that correlate insertion loss to dielectric value of the volume of the material in the tank. The volume of the material may refer to a level if the material is a liquid, slurry, or powder. Alternatively, the level of the material may refer to a density if the material is a gas, for example. As explained above, the database information may be determined using simulations, or may be based on experimental lab work, for example.

In either case, once the control logic has determined an insertion loss value or propagation delay value and inferred a dielectric value and/or composition or volume, a report may be provided 1020 to a higher control level within the system. In the case of the diesel engine example, the results may be reported to an engine control system that may prevent the engine from being started if the correct urea based liquid is not in the tank, for example.

Figure 11:
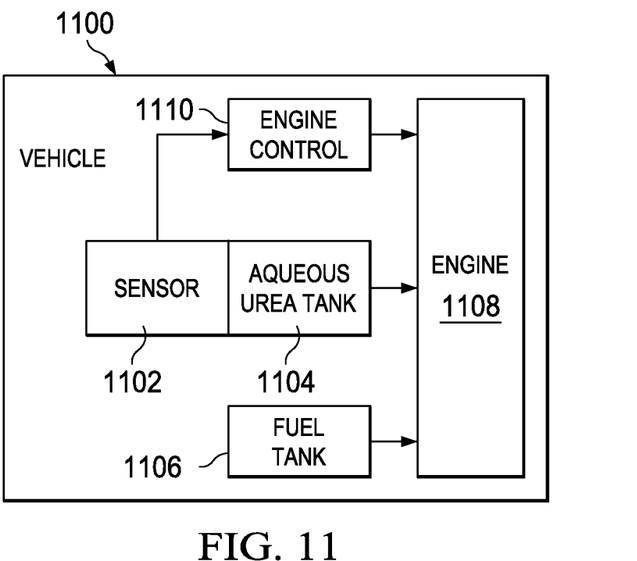
FIG. 11 is a block diagram of a vehicle that includes a composition sensor.

FIG. 11 is a block diagram of a vehicle 1100 that includes a composition sensor 1102 as described herein. Composition sensor 1102 is mounted on a tank 1104 that is intended to hold an aqueous urea solution. Diesel engine 1108 draws diesel fuel from fuel tank 1106 and aqueous urea solution from tank 1104 while it is operating. As described above in more detail, sensor 1102 and related control logic may sense the composition of the liquid within tank 1104 and cause engine control logic 1110 to prevent the engine from starting when a correct solution is not present in tank 1104, for example.

Figure 12:
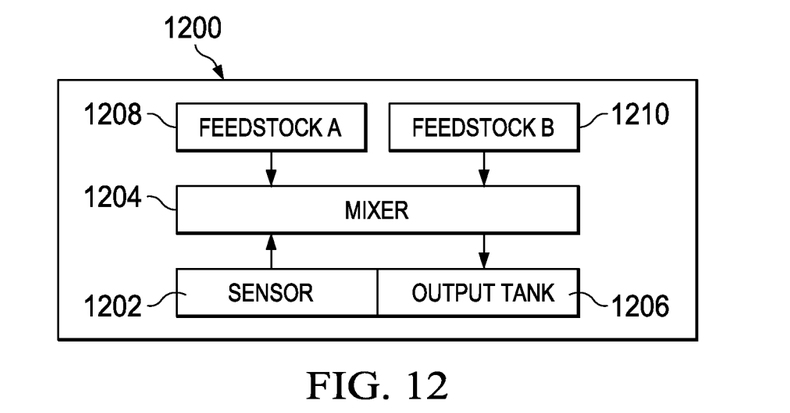
FIG. 12 is a block diagram of a fabrication system that uses a composition sensor to control a fabrication process.

FIG. 12 is a block diagram of a fabrication system 1200 that uses a composition sensor 1202 as described herein to control a fabrication process. Mixer 1204 may draw feedstock from two or more sources 1208, 1210 and combine them to produce an output product that is stored in tank 1206, for example. Sensor 1202 may probe the material as it is stored in tank 1206 and provide feedback to mixer 1204 in real time to control the ratio of feedstock material in order to fabricate a material that is within a preferred composition range, for example.

Figure 13:
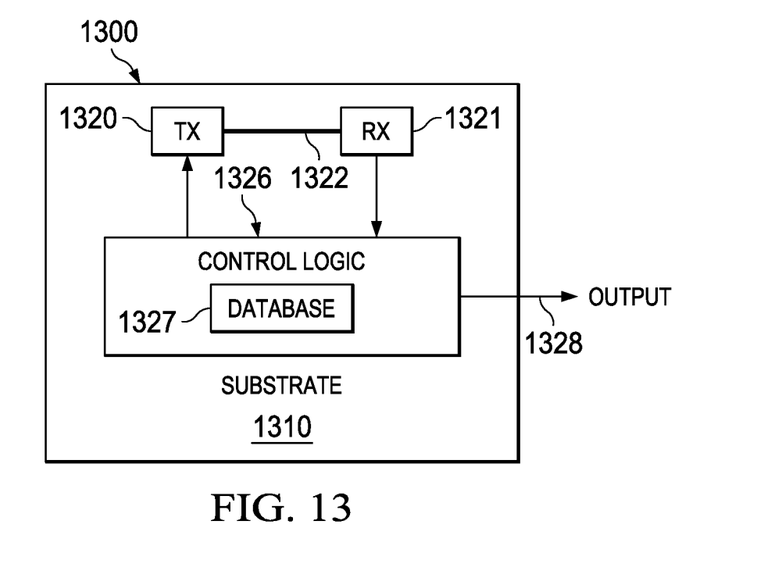
FIG. 13 is an example of a self-contained sensor for detection and analysis of surrounding material.

FIG. 13 is an example of a self-contained sensor 1300 for detection and analysis of surrounding material. In this example, TX 1320 and RX 1321 are mounted on a common substrate 1310. DWG 1322 is coupled between them and may act as a probe for material that is placed in proximity to sensor 1300. In this example, DWG 1320 is fabricated directly on a surface of substrate 1310. This substrate may range from an integrated circuit (IC) die, a substrate in a multi-chip package, a printed circuit board (PCB) on which several ICs are mounted, etc., for example. The substrate may be any commonly used or later developed material used for electronic systems and packages, such as: silicon, ceramic, Plexiglas, fiberglass, plastic, metal, etc., for example. The substrate may be as simple as paper, for example.

Control logic 1326 is controllably coupled to TX 1320 and RX 1321 so that it can determine attenuation that occurs to a signal being propagated through DWG 1322, in a similar manner as described above in more detail. Database 1327 may be loaded with correlation data for insertion loss that has been determined experimentally, by simulation, etc., for example, for a range of materials that the sensor is intended to probe, as described in the examples above.

Sensor 1300 may be sold as a packaged unit and then coupled to a host system, for example. Output 1328 may provide the host system detection and composition information relating to material that is placed in proximity to DWG 1322, for example.

The various DWG configurations described above may be fabricated using a printing process, such as an inkjet printer or other three dimensional printing mechanism. Fabrication of three dimensional structures using ink jet printers or similar printers that can "print" various polymer materials is well known and need not be described in further detail herein. For example, see "3D printing," Wikipedia, Sep. 4, 2014. Printing allows for the rapid and low-cost deposition of thick dielectric and metallic layers, such as 0.1 um-1000 um thick, for example, while also allowing for fine feature sizes, such as 20 um feature sizes, for example. Standard integrated circuit (IC) fabrication processes are not able to process layers this thick. Standard macroscopic techniques, such as machining and etching, typically used to manufacture dielectric waveguides and metallic structures may only allow feature sizes down to 1 mm, for example. These thicker printed dielectric and metallic layers on the order of 100 nm-1 mm which are made possible by inkjet printing enable waveguide operation at Sub-THz and THz frequencies. Previously optical frequencies could be handled using standard semiconductor fabrication methods while lower frequencies may be handled using large metallic waveguides; however, there was a gap in technology for fabricating waveguides for THz signals. Printing the waveguides directly onto the chip/package/board mitigates alignment errors of standard waveguide assemblies and simplifies the packaging process. Formation of a DWG on a substrate is described in more detail in U.S. patent application Ser. No. 14/498,837, entitled "Metallic Waveguide with Dielectric Core", Benjamin Cook, et al, and is incorporated by reference herein.

As described above, using a DWG to detect and analyze the contents of a tank is an extremely sensitive mechanism that uses a very low power electromagnetic signal travelling through a plastic dielectric waveguide. This results in a very safe, sensitive, simple, and cheap detector.

Other Embodiments

While the invention has been described with reference to illustrative embodiments, this description is not intended to be construed in a limiting sense. Various other embodiments of the invention will be apparent to persons skilled in the art upon reference to this description. For example, while a simple rectangular tank was illustrated herein, all manner of shapes and sizes of tanks may be monitored using sensor embodiments described herein. Various configurations and arrangements of one or more DWGs may be configured within the tanks.

Embodiments of a DWG may be fabricated using flexible materials for the core and cladding, as described herein, or may be fabricated using rigid materials such as hard plastic, fiberglass structures, etc., for example.

In some embodiments, a conductive shield may be provided on a portion of the length of a DWG, and not be present on another portion of the DWG. For example, it may be beneficial to probe the material in the tank in only a selected region. In this case, a portion of a DWG may be shielded with a conductive shield.

While a diesel engine system was described herein, embodiments of the invention may be used in a vast array of container applications in which a safe, low cost volume and/or composition sensor is needed.

In some applications, a sensor as described herein may be located in pipe to sense material flowing through the pipe. In another application a sensor as described herein may be used to sense a liquid, slurry, or powder in an open container, such as a mixing vessel, a rail car, etc., for example. In another application a sensor as described herein may be used to sense pollution in a river, reservoir, or lake, for example. In another application a sensor as described herein may be used to sense gases in a room, or even in open space out of doors, for example.

Therefore, within the claims, the term "tank" is understood to refer to any open or closed tank or vessel; any pipe or other conveyance for moving liquids, slurries, etc.; any open body of water or other liquid; etc., for example.

As described herein, the dielectric value of a material may be inferred based on insertion loss to an RF signal as it propagates through a DWG surrounded by the material. Similarly, as described herein the dielectric value of a material may be inferred based on the time of flight an RF signal as it propagates through a DWG surrounded by the material. Therefore, within the claims the term "propagation characteristic" is understood to refer to propagation loss, or to time of flight, for example, of a signal that propagates through a DWG that is at least partially surrounded by the material.

In some applications, sensors as described herein may be used within a feedback loop of a fabrication system to control the results of a mixing or compounding process, for example.

In some applications, sensors as described herein may be used to detect when a liquid or other material is leaking into an area, for example.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection, for example.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A method of detecting a material, the method comprising:
    transmitting a radio frequency (RF) signal through at least a solid dielectric core of a dielectric waveguide (DWG);
    receiving the RF signal after it passes through at least the solid dielectric core;
    determining a propagation characteristic of the RF signal through at least the solid dielectric core; and
    in response to whether the propagation characteristic exceeds a threshold value, detecting whether the material surrounds at least a portion of the DWG.

2. The method of claim 1, further comprising determining a dielectric constant value of the material based on the determined propagation characteristic.

3. The method of claim 2, further comprising determining a composition of the material based on the determined inferred dielectric constant value.

4. The method of claim 1, further comprising determining a composition of the material based on a correlation to the propagation characteristic value.

5. The method of claim 1, further comprising determining an amount of the material based on a correlation to the propagation characteristic.

6. The method of claim 1, wherein the material is contained within a tank.

7. The method of claim 1, further comprising advising a control system about the detecting.

8. The method of claim 4, further comprising advising a control system about the composition of the material.

9. A system comprising a sensor, wherein the sensor comprises:
   a sub-terahertz radio frequency (RF) transmitter with an output;
   a sub-terahertz RF receiver with an input;
   a dielectric waveguide (DWG) having at least a solid dielectric core coupled between the output of the transmitter and the input of the receiver;
   control logic coupled to the receiver, wherein the control logic is coupled to a database that contains a data structure that correlates a propagation characteristic of a signal received by the receiver to a composition of a material surrounding at least a portion of the DWG.

10. The system sensor of claim 9, wherein the control logic is operable to:
   cause the transmitter to transmit a radio frequency signal through at least the solid dielectric core;
   cause the receiver to receive the RF signal after it passes through at least the solid dielectric core;
   determine a propagation characteristic of the RF signal through at least the solid dielectric core; and
   in response to whether the propagation characteristic exceeds a threshold value, detect whether the material surrounds at least a portion of the DWG.

11. The system of claim 10, wherein the control logic is further operable to determine a dielectric constant value of the material based on the determined propagation characteristic.

12. The system of claim 11, wherein the control logic is further operable to determine a composition of the material based on the determined dielectric constant value.

13. The system of claim 10, wherein the control logic is further operable to determine a composition of the material based on a correlation to the propagation characteristic value.

14. The system of claim 10, wherein the control logic is further operable to determine an amount of the material based on a correlation to the propagation characteristic.

15. The system of claim 9, further comprising a tank, wherein at least a portion of the solid dielectric core is within the tank.

16. The system of claim 15, wherein the system is a vehicle having an engine coupled to the tank, and wherein the sensor is operable to provide an alert when the sensor determines that a dielectric constant of a material contained within the tank is outside a predetermined range of values.

17. The system of claim 15, wherein the system is a mixing machine coupled to receive feedstock from two or more sources and to provide an output material to the tank; and wherein the sensor is operable to determine a dielectric value of the output material in real time and to alert the mixer when the dielectric value of the output material is outside a preselected range.

18. The system of claim 9, wherein the transmitter, receiver, DWG and control logic are all located on a single substrate.

19. A method of detecting a material, the method comprising:
   transmitting a radio frequency (RF) signal through at least a solid dielectric core of a dielectric waveguide (DWG);
   receiving the RF signal after it passes through at least the solid dielectric core;
   determining insertion loss of at least the solid dielectric core; and
   determining a composition of the material based on a correlation to the insertion loss value.

20. The method of claim 19, further comprising determining time of flight for a reflected portion of the RF signal; and
   determining a level of the material in the tank based on the time of flight of the reflected portion of the RF signal.

* * * * *